United States Patent [19]
Bearson et al.

[11] Patent Number: 5,907,046
[45] Date of Patent: *May 25, 1999

[54] PROCESSES FOR PREPARING THIOXANTHONE AND DERIVATIVES THEREOF

[75] Inventors: Amy Lisa Bearson; John Robert Ira Eubanks, both of Ocean Springs; Alan Daniel Farmer, Biloxi, all of Miss.; Franklin Dewitt Ford, Grand Bay, Ala.; Diana Boney Haydel, Ocean Springs, Miss.; August John Muller, Mobile, Ala.

[73] Assignee: First Chemical Corporation, Pascagoula, Miss.

[*] Notice: This patent is subject to a terminal disclaimer.

[21] Appl. No.: 08/920,171

[22] Filed: Aug. 25, 1997

Related U.S. Application Data

[63] Continuation of application No. 08/641,165, Apr. 29, 1996, Pat. No. 5,712,401.

[51] Int. Cl.$^6$ ................................................. C07D 335/08
[52] U.S. Cl. .................................................. 549/27
[58] Field of Search ................................ 549/27; 522/53; 525/704, 222

[56] References Cited

U.S. PATENT DOCUMENTS

| | | | |
|---|---|---|---|
| 3,904,647 | 9/1975 | Pfister et al. | 549/27 |
| 4,012,499 | 3/1977 | Hodson et al. | 424/46 |
| 4,101,558 | 7/1978 | Vacek et al. | 549/27 |
| 4,264,773 | 4/1981 | Pigerol et al. | 549/27 |
| 4,321,118 | 3/1982 | Felder et al. | 522/36 |
| 4,450,279 | 5/1984 | Shirosaki et al. | 549/27 |
| 4,661,595 | 4/1987 | Avar | 549/27 |
| 5,177,218 | 1/1993 | Fischer et al. | 549/25 |
| 5,414,092 | 5/1995 | Green et al. | 549/27 |

FOREIGN PATENT DOCUMENTS

| | | |
|---|---|---|
| 2 095 248 | 8/1982 | Germany . |
| 1 595 710 | 8/1981 | United Kingdom . |

OTHER PUBLICATIONS

M.J. Davis et al.; The UV–curing behaviour of some photoinitiators and photoactivators; J. Oil Col. Chem. Assoc. 1978, 61, 256–263.

Dean; "Analytical Chemistry Handbook", pp. 2.116–2.117, section 2.48 (1995).

Chemical Abstracts, vol. 67, No. 21, Nov. 20 1967, Columbus, Ohio, US; abstract No. 99976r, G.E. Ivanov et al.: "Preparation and properties of thioxanthen–9–o1" p.9397; column 1; XP002037812 see abstract & Zh. Org. Khim., vol. 3, No. 6, 1967, pp. 1142–1143.

*Primary Examiner*—Deborah C. Lambkin
*Attorney, Agent, or Firm*—Alston & Bird LLP

[57] ABSTRACT

A process for preparing thioxanthone and derivatives thereof is disclosed. In the process, an aromatic compound, such as cumene, is reacted with thiosalicylic acid (TSA) or dithiosalicylic acid (DTSA) in the presence of sulfuric acid. The reaction mixture, which includes thioxanthone or a derivative thereof, is thereafter distilled under reduced pressure to recover the thioxanthone compound.

17 Claims, No Drawings

PROCESSES FOR PREPARING THIOXANTHONE AND DERIVATIVES THEREOF

This application is a continuation of application Ser. No. 08/641,165, filed Apr. 29, 1996, now U.S. Pat. No. 5,712, 401.

FIELD OF THE INVENTION

The present invention relates generally to processes for preparing compounds useful as polymerization initiators, and more particularly to processes for preparing compounds useful as photoinitiators in photoinduced polymerizations.

BACKGROUND OF THE INVENTION

Thioxanthone and derivatives thereof are recognized as useful intermediates in the preparation of pharmaceuticals and fine chemicals. Such compounds are also useful as photoinitiators or activators for the photopolymerization of unsaturated compounds, which cure or crosslink upon exposure to radiation. These compounds in turn are useful in the production of photocurable surface coatings and inks. Examples of commercially available thioxanthone derivatives useful as photoinitiators include 2-chlorothioxanthone (CTX) and mixtures of 2- and 4-isopropylthioxanthone (ITX).

Conventionally, thioxanthone and its derivatives are prepared by the substitution and cyclization of thiosalicylic acid (TSA) or dithiosalicylic acid (DTSA) with unsubstituted or corresponding substituted aromatic compounds, such as cumene or chlorobenzene, in a concentrated sulfuric acid medium. See, for example, J.O.C. 24, 1914–1916 (1959); J.A.C.S. 74, 4296–4309 (1952); J.C.S. 97, 197; J.C.S. 97, 1290–1299; J.C.S. 1911, 640–649, 1353–1358, 2046–2051; and J.C.S. 1910, 1290–1299.

Known techniques for preparing thioxanthone and derivatives thereof, including isopropylthioxanthone, are not completely satisfactory. These processes can result in low yields of the desired product or result in a mixture of by-products which are difficult to separate by conventional techniques. In addition to low isolated yields, typically large quantities of concentrated sulfuric acid are used and thereafter diluted with water or neutralized with base to free the product during the isolation steps. The disposal of such large amounts of sulfuric acid can be problematic, and the recovery and reuse of spent acid is difficult and costly. Further, filtration of the thioxanthone product from the highly acidic medium can be extremely slow as a result of difficult and time-consuming washing and drying steps. These processing complications can, in turn, adversely affect the quality and cost of the product.

Efforts have been made to address low yields and complicated separation techniques. However, these attempts have resulted in poor quality products having an undesirable dark color. Because thioxanthone and derivatives thereof are widely used as photoinitiators in the ultraviolet ("UV") curing industry, the resultant product should preferably have a very pale yellow to white color and contain minimal or no organic or inorganic insolubles.

Further, in the UV curing industry, advantageously the photoinitiator is readily dissolved in the photopolymerizable systems, which are typically liquid. However, thioxanthone derivatives prepared according to conventional techniques, and in particular ITX, typically are crystalline or powdered solids with low solubility in organic solvents and photopolymerizable systems. Dissolving the compound or preparing a dispersion thereof can, however, add manufacturing steps, increase labor costs, and produce unstable solutions which can polymerize unexpectedly during extended stirring times and heating.

OBJECTS AND SUMMARY OF THE INVENTION

It is accordingly an object of the present invention to provide a process for preparing thioxanthones and derivatives thereof which provide increased isolated yields of the desired product.

It is another object of the present invention to provide a process for preparing thioxanthones and derivatives thereof which provides improved product quality having minimal or no residual organic or inorganic by-products and a desirable color.

It is yet another object of the present invention to provide a process for preparing thioxanthones and derivatives thereof which does not require long, complicated reaction times and schemes to achieve increased yields and/or improved product quality.

It is yet another object of the present invention to provide a process for preparing thioxanthones and derivatives thereof which provides a product which can be readily dissolved in a polymerization system.

These and other objects of the present invention will become apparent from the following general and detailed description of the invention. The objects of the present invention are accomplished by a process for preparing thioxanthone and derivatives thereof wherein a compound of Formula (I)

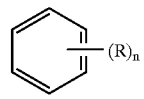

(I)

wherein R is independently selected from the group consisting of H, halogen, C1 to C10 alkyl, C6 to C10 aryl, C7 to C24 alkylaryl, and C1 to C10 alkoxy, and n is 1 to 4, is reacted with thiosalicylic acid (TSA) or dithiosalicylic acid (DTSA) in the presence of sulfuric acid. Preferably, R is C1 to C4 alkyl, more preferably isopropyl, and n is 1.

The reaction results in a reaction mixture which includes as a component thioxanthone or a derivative thereof, having the Formula (II):

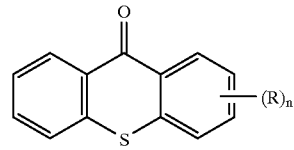

(II)

wherein R and n of Formula (II) are each the same as defined above for Formula (I), i.e., R of Formula (I) and R of Formula (II) are the same moieties and n is the same in Formula (I) and Formula (II). For example, if R of Formula (I) is isopropyl and n is 1, i.e., the compound of Formula (I) is cumene, then the reaction mixture includes as a component thereof a compound of Formula (II), wherein R is also isopropyl and n is 1.

The reaction mixture also includes byproducts in addition to the desired thioxanthone product of Formula (II). For example, the reaction mixture can include spent sulfuric acid and products of sulfuric acid with the aromatic compound of Formula (I), as well as other byproduct sulfur compounds. The resultant reaction mixture can generally be described as a thick, syrupy red to black solution, its dark color attributed in large part to the presence of the various sulfur byproducts.

To recover or purify the thioxanthone product of Formula (II) from the reaction mixture, the thioxanthone product is extracted from the reaction mixture using an appropriate organic solvent. The reaction mixture advantageously is also treated to dilute residual sulfuric acid and other acid byproducts, which can be recovered or disposed.

The organic extract product is then distilled. The inventors have discovered that, contrary to conventional wisdom, compounds of Formula (II) above can be recovered by distilling the organic extract product under conditions of low pressure. Specifically, the compounds of Formula (II) can be recovered by distillation at pressures no greater than about 25 Torr. Distillation temperatures can range up to about 300° C., and preferably range from about 215° C. to about 250° C. Wiped film evaporators, molecular stills or other distillation equipment with short residence times may be operated at higher pressures and temperatures as is known to those skilled in the art.

This is unexpected because these types of compounds, which have relatively high molecular weights, are recognized in the art as having extremely low vapor pressures. Because of their extremely low vapor pressures, these compounds are considered to be essentially non-volatile. Indeed, an extensive review of the literature found 1145 thioxanthone compounds and reported boiling points for only two of those compounds. Thus, one would expect these compounds to decompose at high temperatures, and would not expect that the compounds could be distilled at all, much less that distillation could be an effective technique for recovery or purification of the compounds. Indeed, many of these compounds are reported to decompose at their melting points.

After the distillate is recovered, the thioxanthone compound can be further purified by crystallization. Specifically, a solution is formed of the recovered thioxanthone compound with an organic solvent, and the solution subjected to conditions sufficient to cause the thioxanthone compound to crystalize.

In the process of the invention, thioxanthones and derivatives thereof can be prepared in high isolated yields up to about 75% and higher. Reaction times can be short, and the resultant product can have minimal or no residual organic or inorganic by-products and a desirable color, ranging from a very pale yellow to off-white. Further, the recovered product can be readily dissolved in a polymerization medium.

The present invention also provides photopolymerizable compositions which include a compound of Formula (II) prepared as described above, as well as processes of using the same.

DETAILED DESCRIPTION OF THE PREFERRED EMBODIMENTS

In the present invention, thioxanthone and derivatives thereof are prepared by reacting effective amounts of a compound of Formula (I)

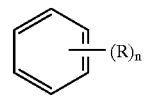

(I)

wherein R is independently selected from the group consisting of H, halogen, C1 to C10 alkyl, C6 to C10 aryl, C7 to C24 alkylaryl, and C1 to C10 alkoxy, and n is 1 to 4, with thiosalicylic acid (TSA) or dithiosalicylic acid (DTSA), preferably DTSA, in the presence of acid, preferably sulfuric acid, to effect substitution and ring closure. Preferably, R is C1 to C4 alkyl, more preferably isopropyl, and n is 1.

Sulfuric acid is preferably used in an amount of about 1 to about 20 parts by weight sulfuric acid per one part by weight of DTSA or TSA. The molar ratios of DTSA to the aromatic compound of Formula (I) can vary from about 1:2 to about 1:10, and molar ratios of TSA to the aromatic compound of Formula (I) can vary from about 1:1 to about 1:5. The concentration of sulfuric acid preferably is greater than about 98%.

Typically, the reactants are charged to a reaction zone and stirred for a time sufficient to insure completion of the reaction. Reaction temperatures during the addition of the reactants typically are in the range of about 15° C. to about 25° C., and can increase during the reaction to about 40° C. to about 90° C. The reaction proceeds for about 0.5 hours to about 3 hours, after which time the reaction mixture can be allowed to cool.

The resultant reaction mixture includes as a component a compound of Formula (II)

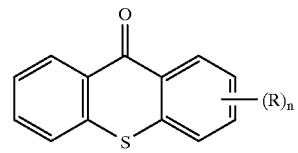

(II)

wherein R is the same as defined above. Specific examples of compounds which can be prepared in accordance with the present invention include, but are not limited to, thioxanthone, 2- and 4-isopropylthioxanthone, 2-chlorothioxanthone, 2-bromothioxanthone, 2-methylthioxanthone, 2-phenylthioxanthone, 2-benzylthioxanthone, 2-acetylthioxanthone, and the like. The process of the invention is particularly useful for the preparation of alkyl substituted thioxanthones, including 2- and 4-isopropylthioxanthone.

The resultant reaction mixture also includes byproducts in addition to the desired thioxanthone compound. The byproducts can include spent sulfuric acid, products of sulfuric acid with the aromatic compound of Formula (I) (i.e., cumene sulfonic acid, when R is isopropyl), as well as other byproduct sulfur compounds. The resultant reaction mixture can generally be described as a thick, syrupy red to black solution, its dark color attributed in large part to the presence of the various sulfur compounds.

The reaction mixture is advantageously treated to dilute the residual sulfuric acid and byproducts, which can then be effectively removed from the reaction mixture and disposed using conventional techniques. Preferably, water is added to the reaction mixture in an amount sufficient to improve extractability of the thioxanthone product. However, the amount of water added should not be so great that the desired thioxanthone product begins to precipitate. Preferably, water is added to the reaction mixture in an amount sufficient to dilute the acid components to a strength of about 50% to about 70%.

The reaction mixture is then extracted into a suitable organic solvent, typically a hydrocarbon such as toluene, benzene, xylenes, cumene, heptane, octane, naphtha, chloroform, methylene chloride, and the like, and the aqueous layer including diluted sulfuric acid and acid byproducts removed, for example, by decantation.

The organic extract product can still include residual sulfuric acid and byproducts. Advantageously, the organic extract product is neutralized with a suitable alkaline agent, such as ammonia, hydroxides of alkali and alkaline earth metals (NaOH, KOH, $Mg(OH)_2$, etc.) and the like, and the resultant aqueous waste layer removed. The organic extract product can be further washed, preferably with water, to remove any residual byproducts and the organic solvent evaporated.

The organic extract product is thereafter distilled under conditions effective to recover or purify the desired thioxanthone compound of Formula (II). Preferably, the organic product is distilled at less than atmospheric pressure, more preferably at a pressure of no greater than about 25 Torr, most preferably about 5 to about 10 Torr. Distillation temperatures can range up to about 300° C., and preferably range from about 215° C. to about 250° C. For example, to recover isopropylthioxanthone, the product can be distilled at a liquid temperature of about 230° C. to about 250° C. at about 5 to about 10 Torr, with the vapor temperature ranging from about 215° C. to about 235° C.

The recovered distillate comprising the thioxanthone compound can be crystallized by flaking, spray drying or other methods known in the art. Preferably, the recovered distillate comprising the thioxanthone compound is crystallized by dissolving the recovered distillate in a suitable solvent. The solution is thereafter subjected to conditions sufficient to form crystallized thioxanthone compound, preferably by cooling the solution and filtering the resultant crystals. Exemplary solvents include ethers, carboxylic acid esters (such as ethyl acetate), ketones, alkanols (methanol, ethanol), cyanides (such as acetonitrile), and mixtures thereof. Preferred solvents are lower alkanols having 1 to 8 carbon atoms, preferably 1 to 4 carbon atoms, and most preferably methanol.

The resultant thioxanthone compound can be isolated in yields up to 75%, and higher, can be substantially free of insolubles, and can display a product quality which greatly exceeds any commercially available product to date.

The thioxanthone compounds of the invention are useful as a component of photopolymerizable compositions as a photoinitiator. As used herein, and as will be appreciated by the skilled artisan, the term photopolymerizable composition refers to compositions which harden or cure upon exposure to radiation.

Generally photopolymerizable compositions include ethylenically unsaturated compounds, including monomers, oligomers, polymers, prepolymers, resinous materials, optionally dispersed or dissolved in a suitable solvent that is copolymerizable therewith, and mixtures thereof, which are photopolymerizable when exposed to a source of ultraviolet ("UV") radiation. As will be appreciated by the skilled artisan, the photopolymerizable compounds can be monofunctional, or can include two or more terminal polymerizable ethylenically unsaturated groupings per molecule.

Exemplary photopolymerizable compounds or precursors include, but are not limited to, reactive vinyl monomers, including acrylic monomers, such as acrylic and methacrylic acids, and their amides, esters, salts and corresponding nitriles. Suitable vinyl monomers include, but are not limited to, methyl acrylate, ethyl acrylate, n- or tert-butylacrylate, isooctyl acrylate, methyl methacrylate, ethylmethacrylate, 2-ethylhexyl methacrylate, butylacrylate, isobutyl methacrylate, the corresponding hydroxy acrylates, i.e., hydroxy ethylacrylate, hydroxy propylacrylate, hydroxy ethylhexyl methacrylate, glycol acrylates, i.e., ethylene glycol dimethacrylate, hexamethylene glycol dimethacrylate, the allyl acrylates, i.e., allyl methacrylate, diallyl methacrylate, the epoxy acrylates, i.e., glycidyl methacrylate, and the aminoplast acrylates, i.e., melamine acrylate. Others such as vinyl acetate, vinyl and vinylidene halides and amides, i.e., methacrylamide, acrylamide, diacetone acrylamide, butadiene, styrene, vinyl toluene, and the like are also included. Prepolymers include acrylated epoxides, polyesters and polyurethanes, and are typically combined with a suitable monomer for viscosity control. The photopolymerizable compounds may be polymerized to form homopolymers or copolymerized with various other monomers.

Another advantage of the thioxanthones prepared in accordance with the present invention is their ready dissolution in appropriate vehicles or carriers to prepare photopolymerizable compositions. This is in contrast to conventional thioxanthone photoinitiators, including conventional ITX, which can be difficult to dissolve. The photoinitiator can be present in the photopolymerizable composition in an amount sufficient to initiate polymerization of photopolymerizable compounds therein upon exposure to ultraviolet radiation. Preferably, the composition includes about 0.2 to about 10 percent by weight photoinitiator, and about 99.8 to about 90 percent by weight photopolymerizable compound, both based on the total weight of the composition.

It can be advantageous to also include as a component of the compositions a coinitiator or synergist, that is, a molecule which serves as a hydrogen atom donor. Coinitiators or synergists are known in the art, and are typically alcohols, tertiary amines or ethers which have available hydrogens attached to a carbon adjacent to a heteroatom. Such co-initiators are typically present in an amount of about 0.2 to about 25 percent by weight based on the total weight of the composition. Suitable compounds include triethanolamine, methyl-diethanolamine (MDEA), ethyldiethanolamine and esters of dimethylamino benzoic acid. These compounds behave as co-initiators or accelerators for the primary photoinitiators and can increase the efficiency and speed of the polymerization process.

In addition, the photopolymerizable compositions may contain polymerization inhibitors, fillers, ultraviolet absorbers and organic peroxides.

The photopolymerizable compositions can be applied or deposited on a surface of a substrate using conventional techniques and apparatus. The composition can be applied as a substantially continuous film; alternatively, the composition can be applied in a discontinuous pattern. Usually the compositions of the invention are fluid at ordinary operating temperatures (between ambient and up to about 60° C.).

The thickness of the deposited composition can vary, depending upon the desired thickness of the resultant cured product. Advantageously, the composition is applied to the substrate surface in an amount sufficient to provide a cured coating having a thickness between about 1 micron and about 5 mils.

Typically, the substrate is coated with the uncured photopolymerizable composition and passed under a ultraviolet providing light beam by a conveyer moving at predetermined speeds. The substrate to be coated can be, for example, metal, wood, mineral, glass, paper, plastic, fabric, ceramic, and the like.

The active energy beams used in accordance with the present invention may be visible light or ultraviolet light or may contain in their spectra both visible and ultraviolet light. The polymerization may be activated by irradiating the composition with ultraviolet light using any of the techniques known in the art for providing ultraviolet radiation, i.e., in the range of 240 nm and 420 nm ultraviolet radiation. The radiation may be natural or artificial, monochromatic or polychromatic, incoherent or coherent and should be sufficiently intense to activate the photoinitiators of the invention and thus the polymerization. Conventional radiation sources include fluorescent lamps, mercury, metal additive and arc lamps. Coherent light sources are the pulsed nitrogen, xenon, argon ion- and ionized neon lasers whose emissions fall within or overlap the ultraviolet or visible absorption bands of the compounds of the invention.

When polymerized by exposure to UV radiation, the compositions give a substantially tack-free product which is durable for ordinary handling. The compositions are useful in any of the types of applications known in the art for photopolymerizations, including as a binder for solids to yield a cured product in the nature of a paint, varnish, enamel, lacquer, stain or ink. The compositions are particularly useful in the production of photopolymerizable surface coatings in printing processes, such as lithographic printing, screen printing, and the like.

The present invention will be further illustrated by the following non-limiting examples.

EXAMPLE 1

Preparation of Isopropylthioxanthone (ITX)

Concentrated sulfuric acid (139 g), DTSA (10 g), and cumene (31.7 g) were charged to a reactor at ambient temperature and then stirred for 0.5 hours. Water (30 g) and toluene (60 g) were added, and the sulfuric acid layer was decanted.

The toluene product layer was neutralized. The aqueous layer was decanted and the toluene layer was washed once with water.

The toluene was evaporated under vacuum and the residue (crude isopropylthioxanthone) was vacuum distilled at a pressure of about 5 Torr and a boiling point of about 231–240° C.

The molten distilled product was dissolved in methanol, cooled, filtered and dried. The ITX product recovered (10.1 g) assayed greater than 99.0%, and had no insolubles when dissolved 10% in toluene, a Gardner color of a 1% solution in toluene less than 1, a bulk density of less than 0.5 g/cc, and a melting range of 67–72° C.

Methanol is particularly advantageous as a solvent, and can be reused indefinitely. This reuse is possible because the distilled ITX does not leave impurities in the methanol. Normally a mother liquor may be reused only a limited number of times before impurities build to an unacceptable level. Reuse of the methanol can decrease cost, and also can increase yield because the methanol fed to each subsequent batch is already saturated with ITX, providing 100% yield for each subsequent crystallization operation.

EXAMPLE 2

Solubility of ITX of the Invention

The rate of solubility of ITX as described in Example 1 above were evaluated and compared to that exhibited by various commercially available thioxanthone photoinitiators.

Rate of Solubility Determinations

200–400 mg of the initiator was weighed accurately in a 20 ml vial. About 10 g of tripropylene glycol diacrylate was then weighed accurately into the vial. A stir bar was introduced into the vial and the solution stirred using a magnetic stirrer. The time taken for complete dissolution of the initiator was noted and the average rate of solubility was calculated as the amount of initiator dissolved per unit time.

Table 1 shows the results comparing the rates of dissolution of these initiators at two different levels, namely, 2 and 4%, which is typical in the majority of practical applications.

TABLE 1

Rates of Dissolution of Thioxanthone Initiators

| Initiator | % | Average Rate of Dissolution (mg/min.) | % | Average Rate of Dissolution (mg/min.) |
|---|---|---|---|---|
| ITX, Invention | 2.0 | 25.2 | 4.0 | 44.8 |
| ITX, Comparative | 2.0 | 16.8 | 4.0 | 28.8 |
| 1-chloro 4-propoxy thioxanthone ("CPTX") | 2 | 10.1 | 4 | 4.9 |
| 2,4 Diethyl thioxanthone ("DETX") | 2.0 | 11.1 | 4.0 | 16.3 |

Table 1 shows that the rate of solubility of ITX prepared in accordance with the present invention is superior to ITX prepared by a conventional process and superior to the other commercial thioxanthones and the difference is more pronounced at higher concentration.

Thus, ITX prepared in accordance with the present invention has the advantage of dissolving faster than the comparative thioxanthones.

EXAMPLE 3

Comparison of Curing Characteristics

Curing characteristics of ITX prepared in accordance with the present invention were also studied to determine the impact the process had, if any, on its curing characteristics. Curing characteristics of ITX prepared in accordance with the present invention were compared with commercially available ITX as follows.

a. Photo Differential Scanning Calorimetry

Photo DSC is a fast and convenient analytical tool for comparing the efficiencies of initiators under identical conditions. The photo DSC's of ITX prepared in accordance with the invention and commercially available ITX shows the two initiators are of the same efficiency.

b. Cure Speed Measurements and Pendulum Hardness

In addition to photo DSC, performances of the two initiators was also compared in practical formulations. Cure speed and pendulum hardness results are shown in Table 2.

TABLE 2

Comparison of Cure Characteristics of ITX Invention and ITX Comparative

| Color of the Coating | Initiator | Cure Speed (ft./min.) | Pendulum Hardness(s) |
|---|---|---|---|
| Blue | ITX, invention | 180.0 | 31.0 |
|  | ITX, comparative | 190.0 | 34.0 |
| Red | ITX, invention | 250.0 | 29.0 |

TABLE 2-continued

Comparison of Cure Characteristics
of ITX Invention and ITX Comparative

| Color of the Coating | Initiator | Cure Speed (ft./min.) | Pendulum Hardness(s) |
|---|---|---|---|
| | ITX, comparative | 240.0 | 29.0 |
| Yellow | ITX, invention | 120.0 | 18.0 |
| | ITX, comparative | 120.0 | 15.0 |

The data of Table 2 demonstrates that the two initiators give similar cure speeds and pendulum hardness values, suggesting that their efficiencies are comparable.

EXAMPLE 4

Yellowness Index Measurements

Thioxanthones are generally considered unsuitable for curing white coatings due to their tendency to impart yellowness to the coating. However, the pale color of ITX prepared in accordance with the present invention prompted a study of its use in curing a white coating.

Yellowness Index Measurements

Yellowness Index (YI) measurements were made using a Datacolor International Microflash 200 D spectrophotometer. Paper panels coated with the white coating were cured at the maximum cure speed possible for each formulation and the YI measured. Measurements were made at three points and the average value reported as the YI.

The results are shown in Table 3.

TABLE 3

Cure Speed and Yellowness Index of
ITX of the Invention in a White Coating

| Photoinitiators | Cure speed (ft./min.) | Yellowness Index |
|---|---|---|
| DEAP + ITX (comparative) + MDEA | 70 | 4.9 |
| DEAP + ITX (invention) + MDEA | 60.0 | 4.5 |

Note: DEAP is 2,2-diethoxyacetophenone.

The data of Table 3 shows that the cure speed of the formulation containing ITX prepared in accordance with the present invention is slightly less than that containing ITX prepared according to a conventional process. However, the yellowing imparted to the coating containing ITX prepared in accordance with the invention is less than that of the coating containing ITX from a conventional process.

The choice of using ITX of the invention as one of the photoinitiators in white coatings can be dependent upon the requirements of a particular application.

EXAMPLE 5

Comparison of ITX of Invention with Commercially Available ITX

Various properties of ITX prepared in accordance with the invention were evaluated and compared to that exhibited by ITX which is currently commercially available and prepared using conventional techniques (designated as A, B, and C below).

The results are set forth below in Table 4.

TABLE 4

Quality Comparison of Isopropylthioxanthone Prepared by Different Processes

| Quality Parameter | A | B | C | Invention |
|---|---|---|---|---|
| Appearance | Yellow powder | Dull Yellow Powder | Pale yellow Powder | Off-white |
| Melting Range | 66–73° C. | Up to 72° C. | 50–76° C. | 67–72° C. |
| Assay | 95%–100% | 96–103% | >98% | 99.2–99.8% |
| Clarity 5–10% in Toluene | Clear/Clean | Ess. Clear | Clear/Clean | Clear |
| Color of Above Solution in Gardner Index | 9 maximum (5% Toluene) | 9 maximum (5% Toluene) | 5–7 (1% Toluene) | 1–2 (5% Toluene) |
| Loss on Drying | 0.5 max. | 0.5 max. | <0.1 | <0.1 |
| Sulphated Ash | | <0.2% | | ND |

As the above examples illustrate, the process of the invention produces ITX having a very pale color. In addition, the rate of dissolution of ITX of the invention is higher than that of ITX produced according to other techniques, as well as other thioxanthone initiators. As a consequence, two of the drawbacks associated with the use of ITX as a photoinitiator have been substantially minimized or eliminated. Photo DSC and cure speed results reveal that the efficiency of ITX of the invention has not suffered due to the improvements made in the manufacturing process. Due to the very low yellowness imparted by ITX of the invention, it has good potential for use in white coatings either alone or in conjunction with other photoinititators.

The foregoing examples are illustrative of the present invention and are not to be construed as limiting thereof. The invention is defined by the following claims, with equivalents of the claims to be included therein.

That which is claimed is:

1. A process for preparing thioxanthone and derivatives thereof, comprising:

reacting effective amounts of a compound of Formula (I)

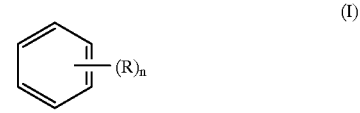

wherein R is independently selected from the group consisting of H, halogen, C1 to C10 alkyl, C6 to C10 aryl, C7 to C24 alkylaryl, and C1 to C10 alkoxy, and n is 1 to 4, with thiosalicylic acid (TSA) or dithiosalicylic acid (DTSA) in the presence of sulfuric acid to form a reaction mixture that includes a substantially non-volatile compound of Formula (II)

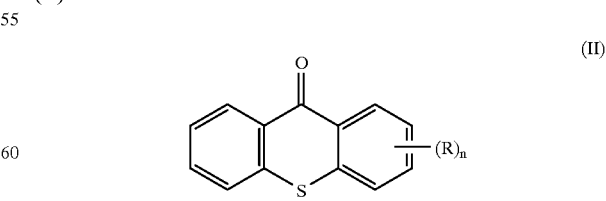

wherein R and n are the same as defined above; and distilling the reaction mixture under conditions sufficient to separate the compound of Formula (II) from the reaction mixture.

2. The process of claim 1, wherein said distilling step is conducted at a pressure less than about 25 Torr.

3. The process of claim 2, wherein R is isopropyl and wherein said distilling step is conducted at a pressure of about 5 to about 10 Torr.

4. The process of claim 1, wherein distilling step is preceded by the step of extracting said compound of Formula (II) from said reaction mixture with an organic solvent to form an organic extract product; and
wherein said distilling step comprises distilling said organic extract product comprising said compound of Formula (II).

5. The process of claim 1, wherein said distilling step is followed by the steps of:
forming a solution of said compound of Formula (II) with an organic solvent;
crystallizing said compound of Formula (II) from said solution; and
recovering said crystallized compound.

6. The process of claim 1, wherein R is C1 to C4 alkyl and n is 1.

7. The process of claim 6, wherein R is isopropyl and n is 1.

8. A product produced in accordance with the process of claim 1.

9. A process for preparing thioxanthone and derivatives thereof, comprising:
reacting effective amounts of a compound of Formula (I)

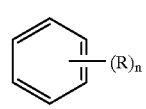

wherein R is independently selected from the group consisting of H, halogen, C1 to C10 alkyl, C6 to C10 aryl, C7 to C24 alkylaryl, and C1 to C10 alkoxy, and n is 1 to 4, with thiosalicylic acid (TSA) or dithiosalicylic acid (DTSA) in the presence of sulfuric acid to form a reaction mixture that includes a substantially non-volatile compound of Formula (II)

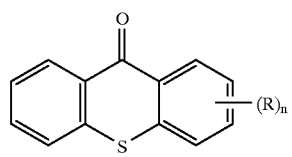

wherein R and n are the same as defined above;
extracting said compound of Formula (II) from said reaction mixture with an organic solvent to form an organic extract product; and
distilling said organic extract product comprising said compound of Formula (II) at a pressure less than atmospheric pressure to separate said compound of Formula (II) from said organic extract product.

10. The process of claim 9, wherein said reaction mixture comprises residual sulfuric acid, and wherein said process further comprises:
diluting said residual sulfuric acid prior to said extraction step; and
separating said diluted sulfuric acid from said organic extract product after said extraction step.

11. The process of claim 9, wherein said distilling step is followed by the steps of:
forming a solution of said compound of Formula (II) with an organic solvent;
crystallizing said compound of Formula (II) from said solution; and
recovering said crystallized compound.

12. The process of claim 9, wherein R is C1 to C4 alkyl and n is 1.

13. The process of claim 12, wherein R is isopropyl and n is 1.

14. A process for preparing isopropylthioxanthone (ITX), comprising:
reacting effective amounts of cumene with thiosalicylic acid (TSA) or dithiosalicylic acid (DTSA) in the presence of sulfuric acid to form a reaction mixture that includes a substantially non-volatile compound of Formula (II)

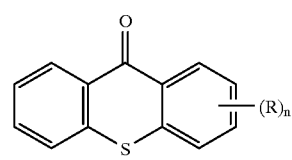

wherein R is isopropyl and n is 1;
extracting said compound of Formula (II) from said reaction mixture with an organic solvent to form an organic extract product; and
distilling said organic extract product comprising said compound of Formula (II) at a pressure less than about 25 Torr to separate said compound of Formula (II) from said organic extract product.

15. The process of claim 14, wherein said reaction mixture comprises residual sulfuric acid, and wherein said process further comprises:
diluting said residual sulfuric acid prior to said extraction step; and
separating said diluted sulfuric acid from said organic extract product after said extraction step.

16. The process of claim 14, wherein said distilling step is followed by the steps of:
forming a solution of said compound of Formula (II) with an organic solvent;
crystallizing said compound of Formula (II) from said solution; and
recovering said crystallized compound.

17. A product produced in accordance with the process of claim 14.

* * * * *